United States Patent
Blanche et al.

(10) Patent No.: US 11,123,577 B2
(45) Date of Patent: Sep. 21, 2021

(54) METHOD AND APPARATUS FOR THE TREATMENT OF CELLULITE WITH THE COMBINATION OF LOW LEVEL LIGHT, ULTRASOUND, AND VACUUM

(71) Applicant: Textural Concepts, LLC, Chatham, NJ (US)

(72) Inventors: Raymond R. Blanche, Chatham, NJ (US); Michael D. Mosk, Oswego, IL (US)

(73) Assignee: Textural Concepts, LLC, Chatham, NJ (US)

( * ) Notice: Subject to any disclaimer, the term of this patent is extended or adjusted under 35 U.S.C. 154(b) by 619 days.

(21) Appl. No.: 15/497,697

(22) Filed: Apr. 26, 2017

(65) Prior Publication Data
US 2017/0304654 A1   Oct. 26, 2017

Related U.S. Application Data

(60) Provisional application No. 62/327,731, filed on Apr. 26, 2016.

(51) Int. Cl.
*A61N 7/00* (2006.01)
*A61H 23/02* (2006.01)
(Continued)

(52) U.S. Cl.
CPC ............... *A61N 7/00* (2013.01); *A61B 18/18* (2013.01); *A61H 23/0245* (2013.01); *A61N 5/0616* (2013.01); *A61B 18/203* (2013.01); *A61B 2017/00734* (2013.01); *A61B 2018/00291* (2013.01); *A61B 2018/00464* (2013.01); *A61B 2018/00994* (2013.01); *A61B 2018/1807* (2013.01); *A61N 2005/0644* (2013.01); *A61N 2005/0649* (2013.01); *A61N 2005/0652* (2013.01); *A61N 2005/0653* (2013.01); *A61N 2005/0659* (2013.01); *A61N 2005/0663* (2013.01); *A61N 2007/0008* (2013.01); *A61N 2007/0034* (2013.01)

(58) Field of Classification Search
CPC .............. A61N 7/00; A61N 2007/0034; A61N 2007/0008; A61H 23/0245; A61B 18/18; A61B 2018/1807
See application file for complete search history.

(56) References Cited

U.S. PATENT DOCUMENTS 6,319,211 B1 * 11/2001 Ito ..................... A61M 1/0047
132/320
6,511,445 B2   1/2003 Sivan
(Continued)

FOREIGN PATENT DOCUMENTS

GB        2261603 A      5/1993

*Primary Examiner* — Sean D Mattson
(74) *Attorney, Agent, or Firm* — McHale & Slavin, P.A.

(57) ABSTRACT

A method and device is taught to improve the appearance of cellulite by combining mild exfoliation of the skin, various wavelengths of low level light, ultrasound, and a vacuum or suction. The device is intended to increase the metabolic rate of the fat cells and reduce their size, while increasing the extensibility or length of the septae. Such increased activity will promote blood flow to the affected area thereby increasing cell nutrients and removing cellular exudates while stimulating the growth of new collagen thereby alleviating the cellulite.

18 Claims, 5 Drawing Sheets

(51) Int. Cl.
*A61N 5/06* (2006.01)
*A61B 18/18* (2006.01)
*A61B 18/00* (2006.01)
*A61B 18/20* (2006.01)
*A61B 17/00* (2006.01)

(56) References Cited

U.S. PATENT DOCUMENTS

| | | | |
|---|---|---|---|
| 6,743,215 B2 | 6/2004 | Bernabei | |
| 6,911,031 B2* | 6/2005 | Muldner | A61B 17/54 |
| | | | 606/131 |
| 7,083,580 B2 | 8/2006 | Bernabei | |
| 2004/0260209 A1 | 12/2004 | Ella | |
| 2004/0260210 A1* | 12/2004 | Ella | A61H 7/008 |
| | | | 601/7 |
| 2005/0251117 A1* | 11/2005 | Anderson | A61B 18/203 |
| | | | 606/9 |
| 2008/0167585 A1* | 7/2008 | Khen | A61B 18/14 |
| | | | 601/6 |
| 2008/0215039 A1 | 9/2008 | Slatkine | |
| 2008/0243039 A1* | 10/2008 | Rhoades | A45D 24/007 |
| | | | 601/73 |
| 2008/0262574 A1 | 10/2008 | Briefs | |
| 2009/0093864 A1 | 4/2009 | Anderson | |
| 2009/0146086 A1* | 6/2009 | Manstein | A61B 18/18 |
| | | | 250/504 R |
| 2010/0274329 A1* | 10/2010 | Bradley | A61N 1/328 |
| | | | 607/90 |
| 2011/0040235 A1* | 2/2011 | Castel | A61F 7/00 |
| | | | 604/20 |
| 2014/0025050 A1 | 1/2014 | Anderson | |

\* cited by examiner

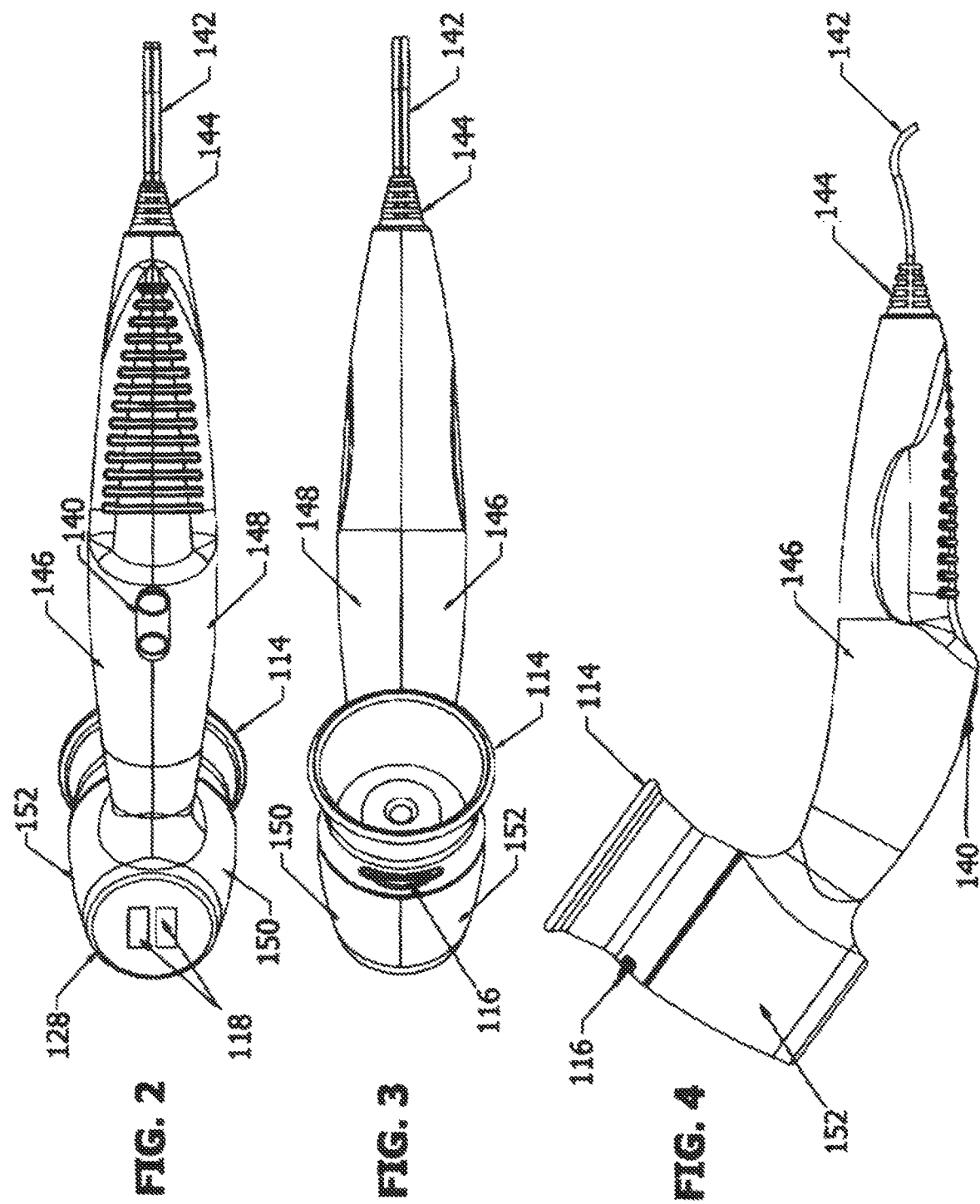

METHOD AND APPARATUS FOR THE TREATMENT OF CELLULITE WITH THE COMBINATION OF LOW LEVEL LIGHT, ULTRASOUND, AND VACUUM

CLAIM OF PRIORITY

This application claims priority to U.S. Application Ser. No. 62/327,731 filed on Apr. 26, 2016, the contents of which are herein fully incorporated by reference in its entirety.

FIELD OF THE EMBODIMENTS

The field of the embodiments of the present invention relate to a method and process to improve the appearance of cellulite by combining mild exfoliation of the skin, various wavelengths of low level light, ultrasound, and mild vacuum.

BACKGROUND OF THE EMBODIMENTS

Cellulite, or dimpling of the skin, is very common, particularly in women, and not always related to excessive weight. Cellulite is a herniation of enlarged subcutaneous fat interspersed with fibrous connective tissue (septae) that gives rise to such dimpling. These enlarged fat cells expand to a point that the connective septae can no longer stretch. This restriction of the septae causes a dimpling effect in the skin which is often called an "orange peel" effect or "mattress" effect. Cellulite may also cause a restriction of blood flow to and out of the affected area, as well as restrictive lymphatic movement. Due to the prevalence in women, and more particularly women of certain races, there are indications that the cause of cellulite is physiological rather than pathological.

Cellulite is hard to treat and cannot be dealt solely with diet and exercise. Treatment for cellulite often requires changing the metabolic processes in the afflicted area(s). There have been attempts to disrupt or change such metabolic processes including devices with rollers that would knead the skin and stretch the skin. However, if the skin was too traumatized by the kneading and rolling, the "treatment" could lead to more adhesions and even exacerbate the appearance of the cellulite.

In response, various thermal elements have been implemented which heat the skin and allow for more efficient stretching of the skin and connective tissues. This approach, while more logical, made treatments even more technique dependent.

Surgical intervention is also an option. In some instances, the surgeon will cut the connective, fibrous septae with a sharp blade or laser. This would instantly remove surface tension created by the shortened, tight septae. However, even this process has downsides as the skin loses some of its "anchoring" to the musculature below and there is an increased risk to create scar tissue. Finally, many topicals (creams) have been produced to address cellulite that fall short of expectations, or fail to show any results, when used as a standalone treatment. Review of related technology:

U.S. Pat. No. 6,743,215 pertains to application of electrical pulses and mechanical vibrations to the skin in a controlled manner, in order to increase the absorption of substances applied previously on the skin. A dermabrasion treatment is first performed on a region of the skin to be later given a skin absorption enhancement treatment. After the dermabrasion treatment, electrical pulses are provided to the skin by way of an array of electrodes disposed on a vibrating head, and the mechanical vibrations are provided to the skin by way of the vibrating head being made to vibrate. Preferably, the electrical and mechanical vibrations are at the same frequency and phase with respect to each other, in order to increase the absorption effect. Also, a suction may be applied to the skin, in order to provide for a substantially uniform absorption of the substance that was applied previously on the skin.

U.S. Pat. No. 6,511,445 pertains to a cellulite massage system that includes a body having a bottom surface, means for producing suction to create a massage action at the bottom surface, and a built-in gel dispenser in said body for dispensing gel to the bottom surface. The invention also provides a method for treating the appearance of cellulite including the steps of applying suction to an area of a body containing cellulite so as to massage that area, and applying gel to that area so as to improve the texture and look of skin on the treated area of the body.

U.S. Patent Application 2014/0025050 pertains to methods and an apparatus for heating up a surface of a skin area that is to undergo a topical treatment. There is a method of placing a device enabled with vacuum suction pressure on a surface of a tissue area to be treated or applying a vacuum suction pressure on the surface of the skin area to pull up the skin area, and an underlying tissue into an aperture opening of the device. Simultaneously, while retaining vacuum suction, the apparatus heats up a volume of tissue that is pulled up inside the aperture opening of the device such that the temperature of the tissue area rises to an elevated ambient temperature and performing a desired treatment, through an energy-generating module, on the tissue volume after the tissue area has been heated up.

U.S. Patent Application 2009/0093864 pertains to methods, systems, and devices to treat a region of skin; the treatment may be used to stimulate the production of collagen or destroy adipose tissue. The region of skin is exposed to a uniform energy application or series of applications. The region of skin may be exposed to positive and negative pressures. Therapeutic substances may be applied to the region of skin.

International Application WO2008/127641 pertains to methods for applying a first and second wavelength of low intensity light therapy to a target area of a subject for various treatments including promoting collagen production, increasing blood flow, decreasing wrinkles, and reducing fat and/or cellulite. The methods can optionally be combined with massaging the tissue or modulating or pulsing the otherwise continuous wave.

Thus, various devices and methodologies are known in the art. However, their structure and means of operation are substantially different from the present disclosure. The other inventions also fail to solve all the problems taught by the present disclosure. At least one embodiment of this invention is presented in the drawings below and will be described in more detail herein.

SUMMARY OF THE EMBODIMENTS

With the physical effects and potential psychological effects of cellulite in mind, a goal of embodiments of the present invention is to increase the metabolic rate of the fat cells and reduce their size, while increasing the extensibility or length of the septae. Such increased activity will promote blood flow to the affected area thereby increasing cell nutrients and removing cellular exudates while stimulating the growth of new collagen.

Thus, the present invention and its embodiments teach and describe an apparatus and method that logically and cost effectively treats cellulite with an "at home" device to be used by the consumer. Its inherent design is safe, easy to use, and a practical way to treat the appearance of cellulite.

The process begins with an exfoliation of the area to be treated. The exfoliation allows an applied topical agent to better penetrate the skin by removing the natural barrier of the stratum corneum. Light sources or light emitting diodes (LEDs) present on the device may then be used on the exfoliated area. The light sources of the device are configured to emit particular wavelength(s) to target particular cell receptors and subcellular mitochondrial components to induce pro-collagen synthesis.

Ultrasound may be used on conjunction with the light sources to create a pathway for the topical agent to better penetrate by increasing cellular permeability. The combination of the energies and chemistry create an effective synergy leading to results that are superior to those known in the art. Further, a vacuum feature of the device may be applied to mechanically yet gently stretch the connective tissue or septae and further increase blood flow to the affected area.

In one embodiment of the present invention there is a cellulite disrupting apparatus having a handle with a first end and a second end; and a head coupled to the first end of the handle, the head having at least a first side and a second side, wherein the first side comprises a cup having a filter positioned therein, the filter being permeable to gases; and wherein the second side comprises a plurality of light sources and at least one ultrasonic transducer.

In another embodiment of the present invention there is a cellulite disrupting apparatus having a handle with a first end and a second end; a head disposed on the first end of the handle, the head having at least a first side and a second side, wherein the first side has a removable cup coupled thereto, and wherein the second side has a plurality of light sources and at least one ultrasonic transducer, wherein the plurality of light sources and the at least one ultrasonic transducer are covered by an optically clear covering; a vacuum port disposed in the first side of the head, wherein the vacuum port is configured to be selectively covered by a filter; and a vacuum tube having a first end and a second end, wherein the first end of the vacuum tube is coupled to the vacuum port and the second end of the vacuum tube is coupled to a motor.

In general, the present invention succeeds in conferring the following, and others not mentioned, benefits and objectives.

It is an object of the present invention to provide an apparatus that stretches or lengthens the septae of a user.

It is an object of the present invention to provide an apparatus allows for transdermal applications of topical creams, ointments, gels, etc.

It is an object of the present invention to provide an apparatus that increases blood flow to a targeted area.

It is an object of the present invention to provide an apparatus that creates a synergistic effect between light therapies and ultrasonic wave therapies.

It is an object of the present invention to provide an apparatus that increases the metabolic rate of subcutaneous fat cells.

It is an object of the present invention to provide an apparatus that is safe and easy to use.

It is an object of the present invention to provide an apparatus that is lightweight and inexpensive.

It is an object of the present invention to provide an apparatus that may be used by the consumer in their home.

BRIEF DESCRIPTION OF THE DRAWINGS

FIG. 2 illustrates a top view of an embodiment of the present invention.

FIG. 3 illustrates a bottom view of an embodiment of the present invention.

FIG. 4 illustrates a side view of an embodiment of the present invention.

DESCRIPTION OF THE PREFERRED EMBODIMENTS

Figure 1:
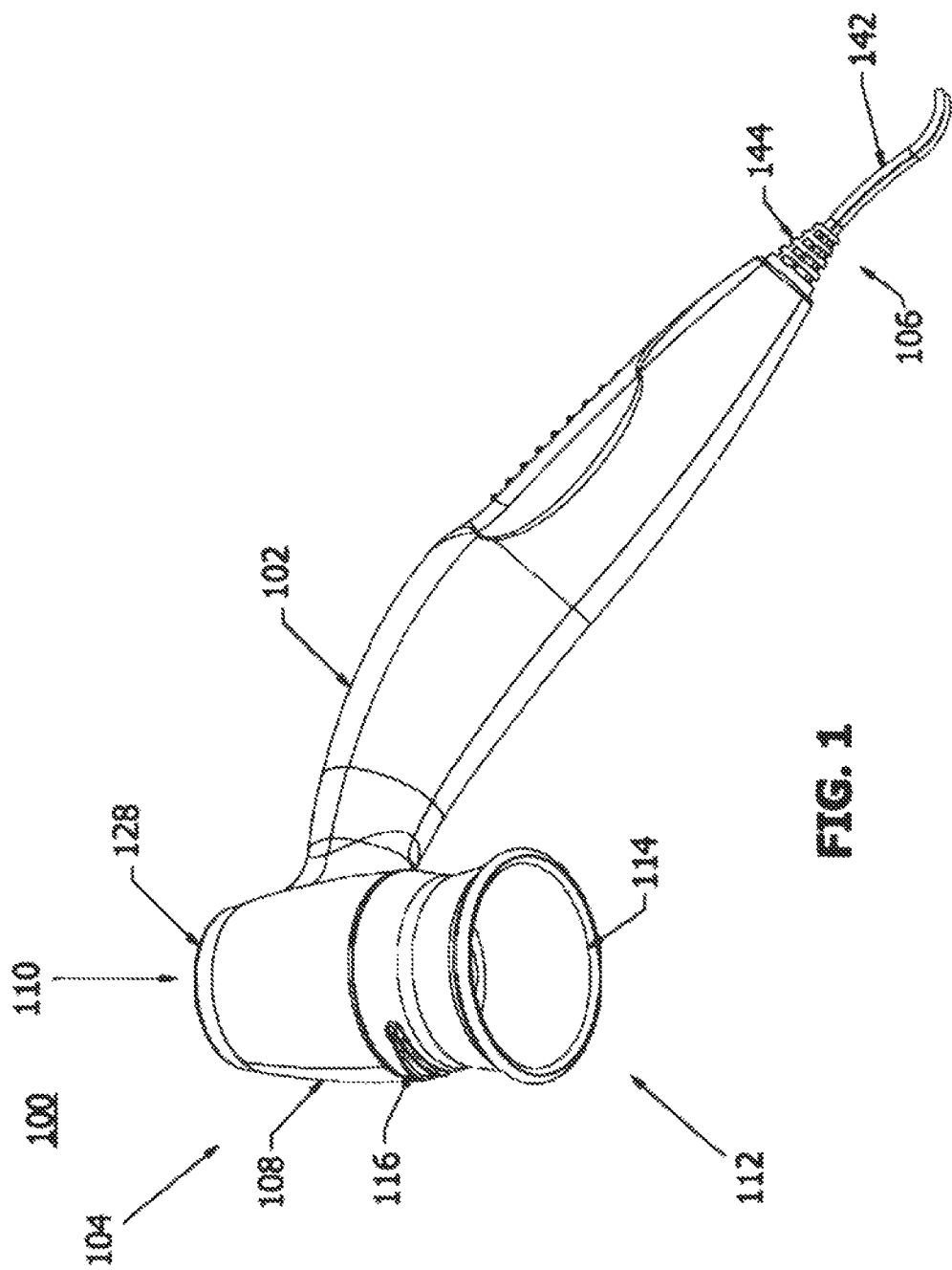
FIG. 1 illustrates a perspective view of an embodiment of the present invention.
Figure 6:
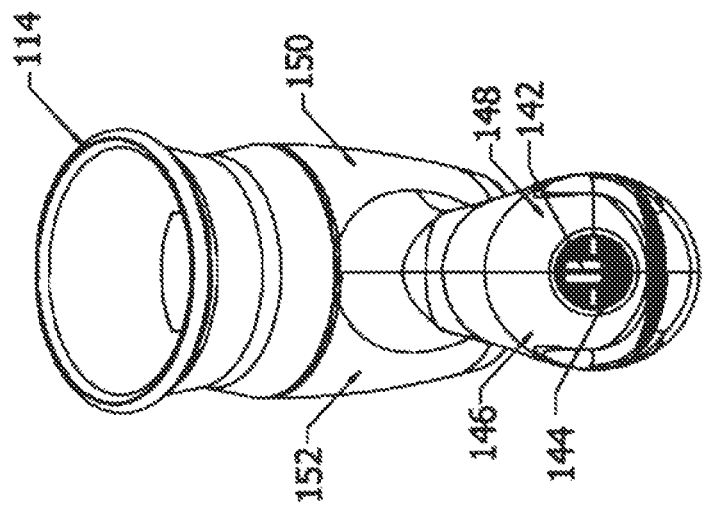
FIG. 6 illustrates a back view of an embodiment of the present invention.
Figure 5:
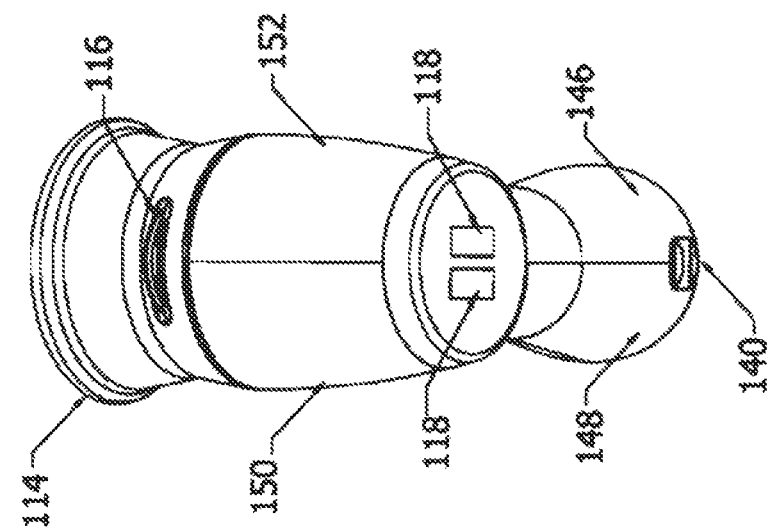
FIG. 5 illustrates a front view of an embodiment of the present invention.

The preferred embodiments of the present invention will now be described with reference to the drawings. Identical elements in the various figures are identified with the same reference numerals.

Reference will now be made in detail to each embodiment of the present invention. Such embodiments are provided by way of explanation of the present invention, which is not intended to be limited thereto. In fact, those of ordinary skill in the art may appreciate upon reading the present specification and viewing the present drawings that various modifications and variations can be made thereto.

Referring now to FIGS. 1-8, there is an embodiment of the present invention. The device 100 generally has a handle 102, a head 108, removable cup 114, bottom 112 of head 108, top 110 of head 108, optically clear covering 128, first end 104, second end 106, power cord 142, power cord anchor 144, filter 116, depressible buttons 140, light sources 120, ultrasonic transducer 118, left side 150 of head 108, right side 152 of head 108, main printed circuit board 136, button printed circuit board 138, left side 148 of handle 102, slot 124, right side 146 of handle 102, vacuum motor 122, vacuum tube 134, and vacuum port 130.

The handle 102 may be generally smooth and polygonal or may be ergonomically configured to support a hand gripping said handle 102. For example, there may be ergonomic finger placement areas to facilitate grip and ease of use. The handle 102 may also have switches or buttons 140 (see FIG. 7) that control its operational state. Such buttons 140 may allow one to change operational modes of the device 100 as well as control its on/off state.

The head 108 may be configured to be dual sided in that each side (top 110, bottom 112) of the head 108 may have operational components. In some embodiments, the functional components are all located on a single side of the head 108, and in other embodiments, the functional components may be located on more than two sides (e.g. top, side, bottom, etc.). The functional components may comprise but are not limited to light sources 120, ultrasonic crystals (transducers) 118, vacuums (see vacuum tube 134 and motor 122 in FIG. 7), filters 116, and the like.

Further, the head 108 is configured to pivot in relation to the handle 102 as pressure is applied to the device 100 as well as contours of the surface to which the device 100 is applied change. The head 108 may be able to pivot up/down (vertically) and side to side (horizontally).

Depending on the pivot mechanism used, vertical and horizontal movement may be achieved simultaneously.

As described herein, it is preferable to use a topical agent or other liquid type agent in conjunction with the treatment device 100. As such, the vacuum feature has a foam based filter 116 to prevent suctioning of the topical agent into the device 100 thereby preventing the device 100 from becoming damaged. Such foam may be a polyethylene or other suitably dense foam that freely permits the passage of air or gasses (to create suction) while preventing the uptake of the generally liquid, gel, or amorphous topical agent(s).

Figure 7:
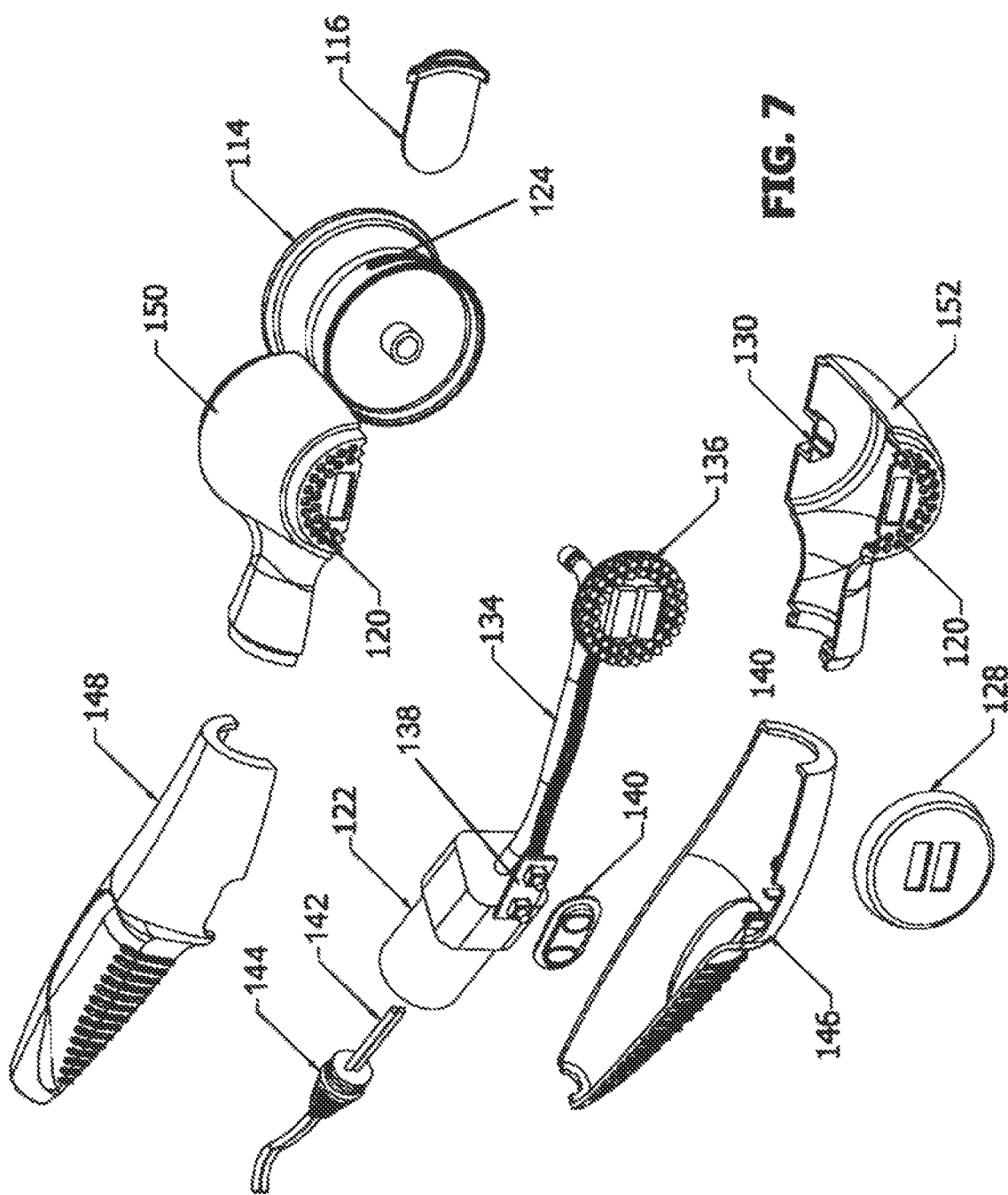
FIG. 7 illustrates an exploded parts view of an embodiment of the present invention.
Figure 8:
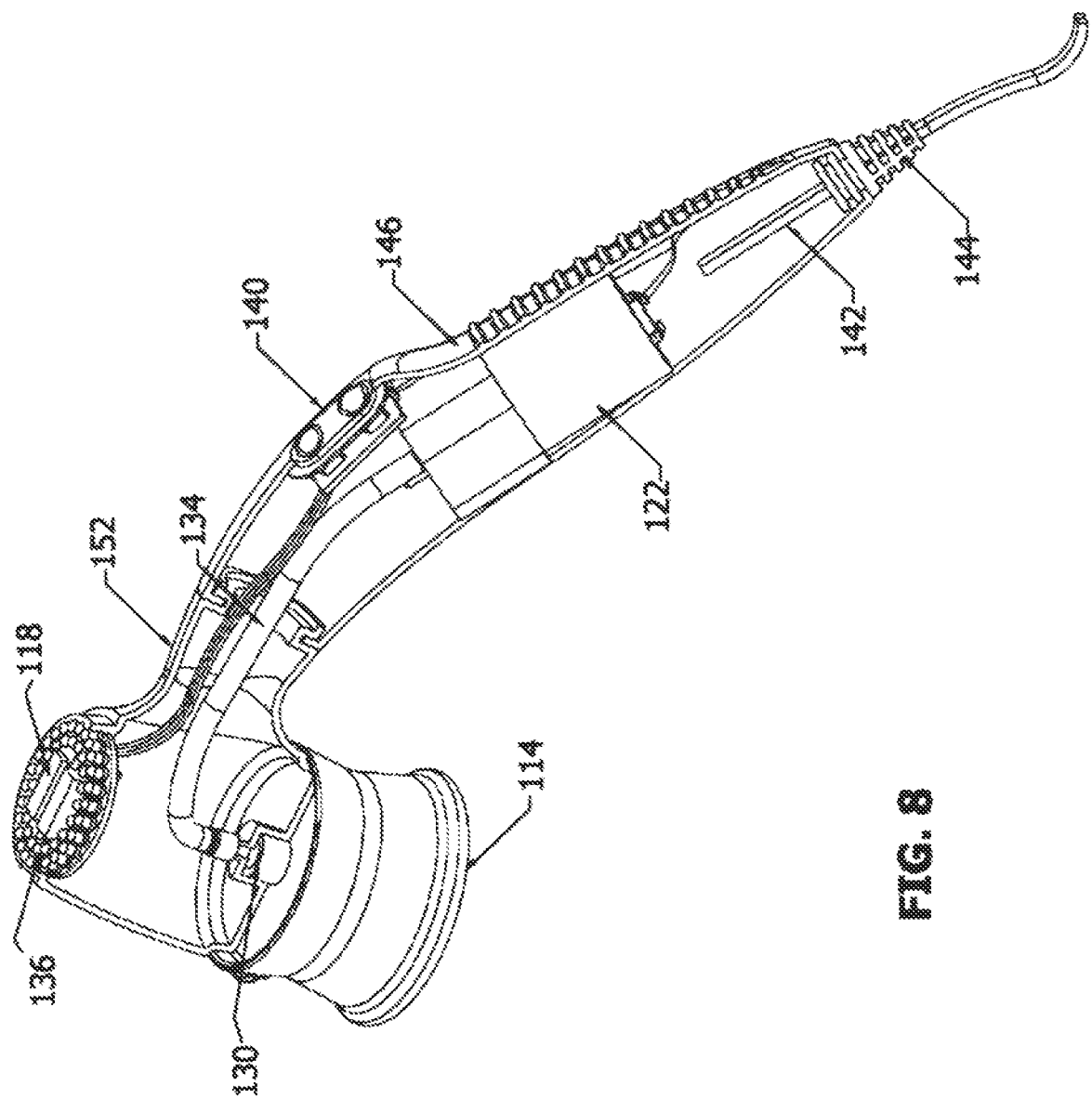
FIG. 8 illustrates a cross-sectional view of an embodiment of the present invention.

The vacuum structures, as shown cross sectionally in FIG. 8, are on the bottom 112 of the head 108 and the ultrasonic transducer 118 and light sources 120 are located on a top 110 of the head 108. The vacuum side of the head 108 has a removable cup 114 to allow suction created by the vacuum (motor 122) to draw tissue upwards into and past the bottom plane of the removable cup 114. The removable cup 114 further has a slot 124 (see FIG. 7), via which the filter 116 can be removed or positioned to cover the vacuum port 130. The filter 116 may cover all or some of the port(s) and may be configured/shaped to the size and shape of the removable cup 114. Further, conventional locking mechanisms may be used to retain the filter 116 once positioned within the slot 124.

The edges or bottom perimeter of the removable cup 114 are rounded to promote a smooth sliding or movement across a skin surface. In some embodiments, additional external structures such as bearings may be used to facilitate the smooth movement across the skin surface. In some embodiments, a retaining ring may be coupled or uncoupled to this perimeter to allow for changing of the filter 116 and other maintenance of the device.

Behind the filter 116, there may be at least one and preferably a plurality of vacuum holes or ports 130 via which suction or a vacuum is created. The ports 130 are positioned to create sufficient suction of the skin while, in some embodiments, further holding the filter 116 in position. In some embodiments, a user may be able to activate or deactivate certain areas of the vacuum and the ports 130 therein to create a custom suction pattern and treatment. The vacuum may be created by a motor 122 contained within the device 100 or may require connection to such a motor or suction creating device. The device 100 may operate of a standard line voltage (power cord 142 and power cord anchor 144) or may other power sources including rechargeable or non-rechargeable batteries.

On a top surface 110 of the head 108 of the device 100 may be the ultrasonic transducer 118 and a light source array comprising a plurality of light sources 120. The ultrasonic transducer 118 may be configured to emit waves at a frequency of about 90 kc to about 950 kc. The light sources 120, as noted, may be any number and type of light emitting device including but not limited to LEDs, OLEDs, and the like. In a preferred embodiment, LEDs are utilized and emit light in a range of about 625 nm to about 725 nm and more preferably about 660 nm. Further light sources 120 may be employed that emit light in a range of about 900 nm to about 1000 nm and more preferably about 950 nm. In some embodiments, the light sources 120 and ultrasonic transducer 118 are operational simultaneously, whereas in other embodiments the light sources 120 and ultrasonic transducer 118 operate singularly.

As shown in FIG. 7, the light sources 120 may be arranged in an array comprising about twelve LEDs configured to emit a "red" wavelength of light and about twelve LEDs configured to emit a "near infrared" (IR) wavelength of light. In other embodiments, there may be as few as four light sources 120 or as many as fifty light sources 120 comprising each wavelength type. Each of the types of light sources 120 may be clustered, linearly arranged, or otherwise arranged to provide coverage to the user as needed. In some embodiments, the light sources 120 are interspersed with one another and each light source 120 emits a particular wavelength of light which may be the same or different as the light sources 120 directly proximate to it.

Further, the light sources 120, as shown in FIG. 7, may be coated or covered in an epoxy or other optically clear covering 128. This protects the light sources 120 and ultrasonic transducer 118 while still allowing the light sources 120 to be effective. It is preferable that any epoxy used is an optically clear epoxy to prevent interference with the light emitted by the light sources 120.

The present treatment device 100 may also be used in various methodologies to form treatment regiments for people afflicted with cellulite. The precise methodology used may depend on the user's needs as well as the device/topical agent parameters and qualities. Below is described but one of the methodologies that may be employed with the present invention. The below methodology is presented for exemplary purposes only and is not intended to limit the scope of the potential methodologies employed.

In a first step, a user may gently exfoliate the stratum corneum of the skin in the area to be treated. This will allow a proprietary or other topical agent to better penetrate the desired treatment area. Various exfoliates may include but are not limited such topicals as a pumpkin scrub, about 10% glycolic foam, or any other degreasing chemical or mechanical agent.

In a second step, a user may apply the topical agent which contains ingredients to achieve localized fatty breakdown, stimulate cellular metabolism, increase blood flow, reduce tissue inflammation and stimulate collagen. In one embodiment, the topical agent is a phosphatidylcholine based agent. The user may then apply the side of the head of the device with the light sources and ultrasound transducer to the skin. It is preferable that the user keep contact with the skin and slide the device slowly over the treatment area until the topical has fully absorbed by the skin.

In a third step, a user may apply the vacuum side of the device to the skin to achieve a gentle suction of the skin surface and underlying tissues into the device while keeping enough lubricant on the skin to gently slide or glide the device around the treatment area. This gentle manipulation of the tissue will assist in increasing the extensibility and/or length of the connective septae.

Although this invention has been described with a certain degree of particularity, it is to be understood that the present disclosure has been made only by way of illustration and that numerous changes in the details of construction and arrangement of parts may be resorted to without departing from the spirit and the scope of the invention.

What is claimed is:

1. A cellulite disrupting apparatus comprising:
a handle having a first end and a second end; and
a head having at least a first side and a second side and pivotally coupled to the first end of the handle, the head being capable of pivoting vertically, horizontally, or vertically and horizontally, as pressure is applied to said apparatus or as a contour of a surface said apparatus is applied thereto is changed,
wherein the first side comprises a cup having a filter positioned therein, the filter being permeable to gases and impermeable to liquids or gels and a motor configured to generate a suction within said cup, which when applied to said surface, draws said surface upwards into and past a bottom plane of said cup free of an encumbrance; and wherein the second side comprises a plurality of light sources and at least one ultrasonic transducer.

2. The apparatus of claim 1 further comprising a slot in the cup, wherein the filter is coupled to the apparatus via the slot.

3. The apparatus of claim 1 wherein the filter is impermeable to solids and semi-solids.

4. The apparatus of claim 1 wherein the at least one ultrasonic transducer and the plurality of light sources are covered by an optically clear covering.

5. The apparatus of claim 1 wherein the cup is removable.

6. The apparatus of claim wherein said plurality of light sources emit light in the range of about 625 nm to about 725 nm or about 900 nm to about 1000 nm.

7. The apparatus of claim 6 wherein said plurality of light sources emit light having the same wavelengths.

8. The apparatus of claim 6 wherein one or more of said plurality of light sources emit light in the range of about 625 nm to about 725 nm and one or more of said plurality of lights emit light in the range of about 900 nm to about 1000 nm.

9. The apparatus of claim 1 wherein said plurality of light sources and said at least one ultrasonic transducer are configured to operate simultaneously.

10. The apparatus of claim 1 wherein said plurality of light sources and said at least one ultrasonic transducer are configured to operate at different times.

11. A cellulite disrupting apparatus comprising:
a handle having a first end and a second end; and
a head disposed on the first end of the handle, the head having at least a first side and a second side,
wherein the first side has a removable cup coupled thereto, said removable cup having an interior portion arranged to receive a surface, and
wherein the second side has a plurality of light sources and at least one ultrasonic transducer,
wherein the plurality of light sources and the at least one ultrasonic transducer are covered by an optically clear covering;
a vacuum port disposed in the first side of the head, wherein the vacuum port is configured to be selectively covered by a filter; and
a vacuum tube having a first end and a second end, wherein the first end of the vacuum tube is coupled to the vacuum port and the second end of the vacuum tube is coupled to a motor, said motor configured to generate a suction within said removable cup, which when applied to said surface, draws said surface into and past a bottom plane of said removable cup free of an encumbrance.

12. The apparatus of claim 11 wherein the plurality of light sources are arranged in a circular configuration around the at least one ultrasonic transducer.

13. The apparatus of claim 11 further comprising a slot in the removable cup, wherein the slot is configured to receive the filter.

14. The apparatus of claim 11 wherein said plurality of light sources emit light in the range of about 625 nm to about 725 nm or about 900 nm to about 1000 nm.

15. The apparatus of claim 14 wherein said plurality of light sources emit light having the same wavelengths.

16. The apparatus of claim 14 wherein one or more of said plurality of light sources emit light in the range of about 625 nm to about 725 nm and one or more of said plurality of lights emit light in the range of about 900 nm to about 1000 nm.

17. The apparatus of claim 11 wherein said plurality of light sources and said at least one ultrasonic transducer are configured to operate simultaneously.

18. The apparatus of claim 11 wherein said plurality of light sources and said at least one ultrasonic transducer are configured to operate at different times.

* * * * *